United States Patent
Hassler et al.

(10) Patent No.: US 7,993,294 B2
(45) Date of Patent: Aug. 9, 2011

(54) WRIST ORTHOSIS

(75) Inventors: Andreas Hassler, Rohrdorf (DE); Gero Hopmann, Neubiberg (DE); Julian Botsch, Trostberg (DE)

(73) Assignee: OPED AG, Steinhausen (CH)

( * ) Notice: Subject to any disclaimer, the term of this patent is extended or adjusted under 35 U.S.C. 154(b) by 786 days.

(21) Appl. No.: 11/630,047

(22) PCT Filed: May 18, 2005

(86) PCT No.: PCT/EP2005/005382
§ 371 (c)(1),
(2), (4) Date: Jan. 2, 2008

(87) PCT Pub. No.: WO2005/122974
PCT Pub. Date: Dec. 29, 2005

(65) Prior Publication Data
US 2008/0208093 A1     Aug. 28, 2008

(30) Foreign Application Priority Data

Jun. 18, 2004  (DE) .......................... 10 2004 029 457

(51) Int. Cl.
*A61F 13/00* (2006.01)
(52) U.S. Cl. ................................. 602/21; 602/5; 602/20
(58) Field of Classification Search .......... 602/5, 20–22, 602/60–64; 128/882, 877–879; D24/192, D24/190–191
See application file for complete search history.

(56) References Cited

U.S. PATENT DOCUMENTS

| 4,657,003 A | 4/1987 | Wirtz |
| 5,205,812 A | 4/1993 | Wasserman |
| 5,286,249 A | 2/1994 | Thibodaux |
| 5,637,078 A * | 6/1997 | Varn ............................... 602/21 |
| 6,165,148 A | 12/2000 | Carr-Stock |
| 2008/0200855 A1* | 8/2008 | Pomeroy et al. ................. 602/16 |
| 2009/0054820 A1* | 2/2009 | Weltner et al. ................... 602/21 |

FOREIGN PATENT DOCUMENTS

| DE | 44 23 755 A1 | 1/1995 |
| DE | 43 26 751 C2 | 2/1995 |
| DE | 196 51 912 A1 | 6/1998 |
| EP | 0 713 691 A2 | 5/1996 |
| GB | 2 184 659 A | 7/1987 |
| JP | 09-220245 | 8/1997 |
| JP | 2003-522594 | 7/2003 |
| WO | WO 92/04880 | 4/1992 |
| WO | WO 95/33428 | 12/1995 |
| WO | WO 01/60289 A1 | 8/2001 |
| WO | WO 03/055422 A1 | 7/2003 |
| WO | WO 03/082161 A1 | 10/2003 |

OTHER PUBLICATIONS

Office Action for co-pending Japanese Patent Application No. 2007-515802, dated Nov. 26, 2010, pp. 2 total.

* cited by examiner

*Primary Examiner* — Kim M Lewis
(74) *Attorney, Agent, or Firm* — Blakely, Sokoloff, Taylor & Zafman LLP.

(57) ABSTRACT

Wrist orthosis (11) having a supporting shell (10) that is open in the radial direction for receiving the distal forearm area and having a volar hand support (29) for coming into contact with the palmar surface of the hand and having a closing device (31, 32, 33, 70) for force-locking connection of the wrist orthosis to the wrist area, wherein a dimensionally stable supporting insert that surrounds the wrist area and is designed to conform to the forearm area is provided for lining the supporting shell (10), the supporting insert extending beyond the supporting shell (10) starting from a forearm part with a metacarpal part (73) covering the metacarpal area.

12 Claims, 8 Drawing Sheets

WRIST ORTHOSIS

CROSS-REFERENCE TO OTHER APPLICATIONS

This is a National Phase of International Application No. PCT/EP2005.005382, filed on May 18, 2005, which claims priority from German Patent Application No. 10 2004 029 457.7, filed on Jun. 18, 2004.

BACKGROUND OF THE INVENTION

The present invention relates to a wrist orthosis having a supporting shell open in the radial direction to receive the distal forearm area and a volar hand support for coming into contact with the palmar surface of the hand and having a closing device for force-locking connection of the wrist orthosis to the wrist area.

Wrist orthoses of the type defined above are used for stabilizing the wrist as is required after fractures of the radius near the wrist, for example. Immobilizing the wrist area, necessitating involvement of the adjacent areas, i.e., the distal forearm area and the metacarpal area, has proven to be problematical especially with regard to the metacarpal area because in addition to actually immobilizing the metacarpal area, one of the goals is to preserve mobility of the finger joints. With regard to this complex requirement, the design of the orthosis in this transitional area has proven to be especially difficult because achieving mobility of the finger joints must not be associated with inadequate immobilization of the metacarpal area on the distal edge of the orthosis.

The object of the present invention is therefore to propose a wrist orthosis which permits a comfortable immobilization of the metacarpal area with respect to the wrist while nevertheless allowing mobility of the finger joints, especially in the transitional area between the wrist and the metacarpal area.

This object is achieved by a wrist orthosis having the features of Claim 1.

SUMMARY OF THE INVENTION

The inventive wrist orthosis has a dimensionally stable supporting insert that surrounds the wrist area and is designed to conform to the forearm area for lining the supporting shell, extending beyond the supporting shell in the wrist area, starting from a forearm part with a metacarpal part that covers the metacarpal area.

The design of the wrist orthosis in the metacarpal area as a dimensionally stable supporting insert that surrounds the wrist area and is designed to conform to the forearm area allows a sufficiently rigid design for immobilization of the wrist. Then the dimensional stability required for the supporting effect can be defined via dimensionally elastic restoring forces of the supporting insert or a dimensionally rigid design of the supporting insert since complete dimensional rigidity of the supporting insert is not necessary in all cases because of the supporting effect of the volar hand support. The radial pressure on the lining which is necessary to immobilize the wrist area is achieved by means of the supporting shell.

The shape-conforming and thus especially tight support thus achieved through the supporting insert ensures that the implementation of the mobility of the finger joints in the open end or in the edge area of the orthosis is not associated with any play between the orthosis and the metacarpal area.

It is especially advantageous when the metacarpal area of the supporting insert is provided with a device for fixational alignment of the molded cushion insert on the thumb, so that fixational alignment via the thumb can be used as an inertial point for the alignment of the wrist orthosis.

In a possible embodiment of the wrist orthosis, the supporting insert is made of an elastic plastic material. Depending on the type and position of the fracture in the wrist area, the supporting effect created with the plastic material may prove to be adequate.

In another possible embodiment of the wrist orthosis, the supporting insert is made of an evacuable molded cushion insert having a molded body filling consisting of a plurality of molded bodies. This permits a design of the supporting insert that has an extremely high dimensional stability while nevertheless conforming closely to the wrist.

An embodiment of the supporting shell which allows effective volar and dorsal pressure to act upon the distal forearm area with high contact comfort at the same time advantageously consists of providing the supporting shell with a supporting area designed continuously in the ulnar direction with at least one strap proceeding toward the dorsal and volar directions.

It has proven to be especially advantageous for an accurate volar positioning as well as accurate adjustment of the flexion of the hand if the supporting shell is provided with a cantilevered part that is adjustable in its relative arrangement on the distal end for arranging the volar hand support.

If in addition the cantilevered part is arranged so that it is pivotable on the supporting shell with a pivot axis running essentially coaxially with the axis of dorsal flexion, then the cantilevered part allows an adjustment of the dorsal flexion that is adapted to the patient's anatomy.

Depending on the type of injury to be treated in the area of the wrist, e.g., in particular in a case of a distal fracture of the radius, it may prove advantageous to provide an open complementary shell in the direction of the ulna for circular supplementation of the supporting shell, said complementary shell having a supporting area designed to be continuous in the radial direction with at least one strap leading away from it in the dorsal and volar directions and being connectable in a force-locking manner to the supporting shell. Due to the circular supplementation of the supporting shell, the distal radius area in particular is supported more strongly in a reinforcing manner.

An especially compact embodiment of the wrist orthosis, which is supplemented by the complementary shell to form a circular design, is made possible if, for force-locking connection of the complementary shell to the supporting shell, an at least partial overlap is provided between at least one pair of straps comprising a dorsal strap and a volar strap of the supporting shell and a pair of straps comprising a dorsal strap and a volar strap of the complementary shell, the closing device of the supporting shell serving to secure the overlap.

Further stabilization of the overlap may be accomplished if an engagement is designed for producing the overlap between the pairs of straps, such that the straps of the supporting shell engage in a strap guide designed on the straps of the complementary shell or vice versa.

An increase in the functionality of the complementary shell is achieved if the complementary shell has at least two pairs of straps, whereby the proximal pair of straps serves to establish the engaging connection and a dorsal and/or volar strap of a distal pair of straps is provided with a pressing device which has a compressive force adjustment.

It is thus possible in this way to adjust an increased compressive force, in particular in the case of a fracture of the distal ulnus or radius in the immediate fracture area, thus making it possible to simulate the "after-pressure" of the plaster cast, which is known from conventional plaster casts.

An even more precise simulation of this "after-pressure" is made possible when the position of the pressing device is variable relative to the strap.

An effective embodiment of the pressing device which has a simple construction and at the same time ensures a high level of operating reliability is connected to the strap in a manner that is radially displaceable.

BRIEF DESCRIPTION OF THE DRAWINGS

A preferred embodiment of the wrist orthosis is explained in greater detail below with reference to the drawings.

They show.

DETAILED DESCRIPTION OF THE INVENTION

Figure 1:
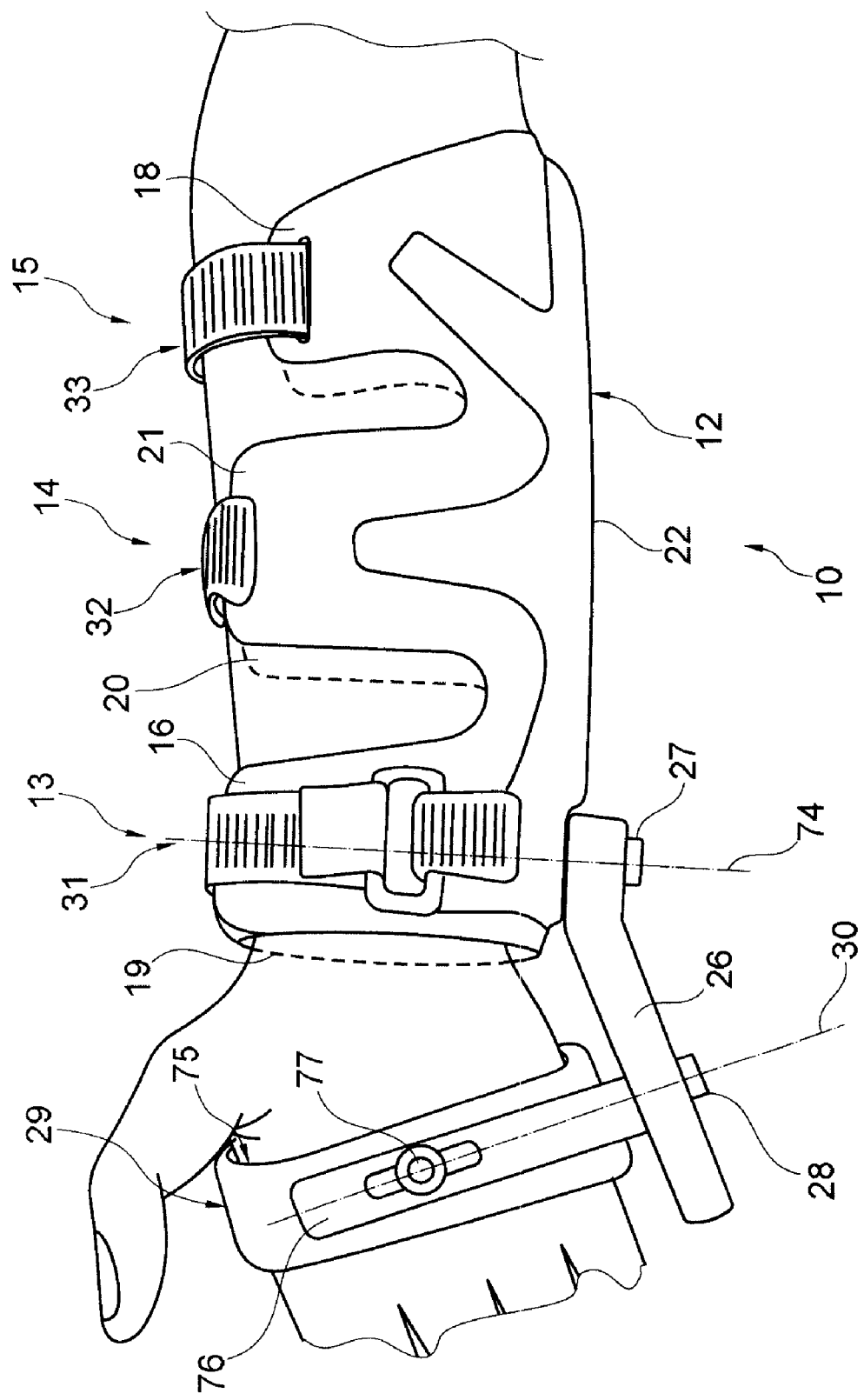
FIG. 1 a supporting shell of the wrist orthosis with a hand support in a volar view.
Figure 6:
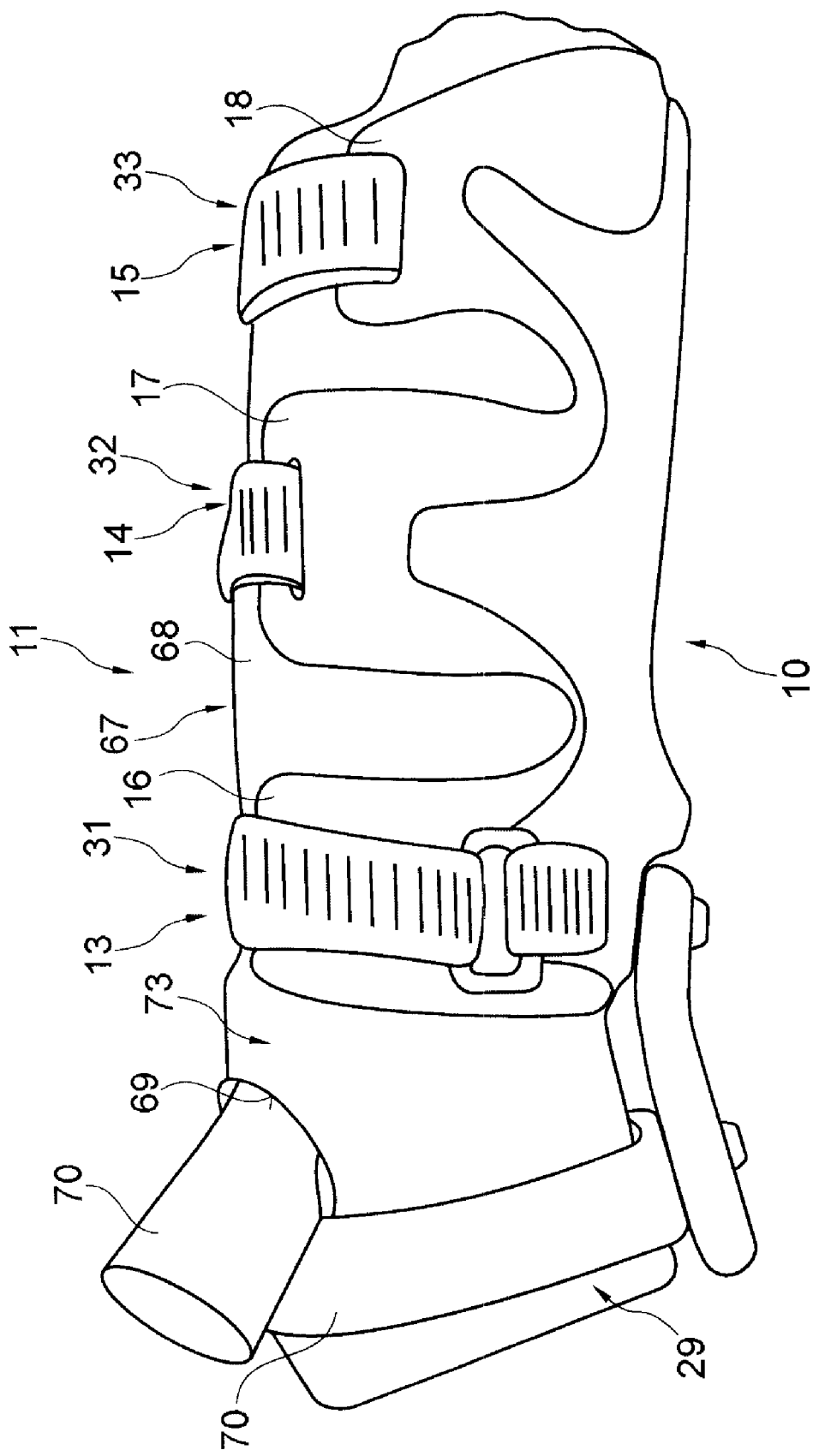
FIG. 6 a wrist orthosis consisting of a supporting shell with a molded cushion insert in a volar view.
Figure 7:
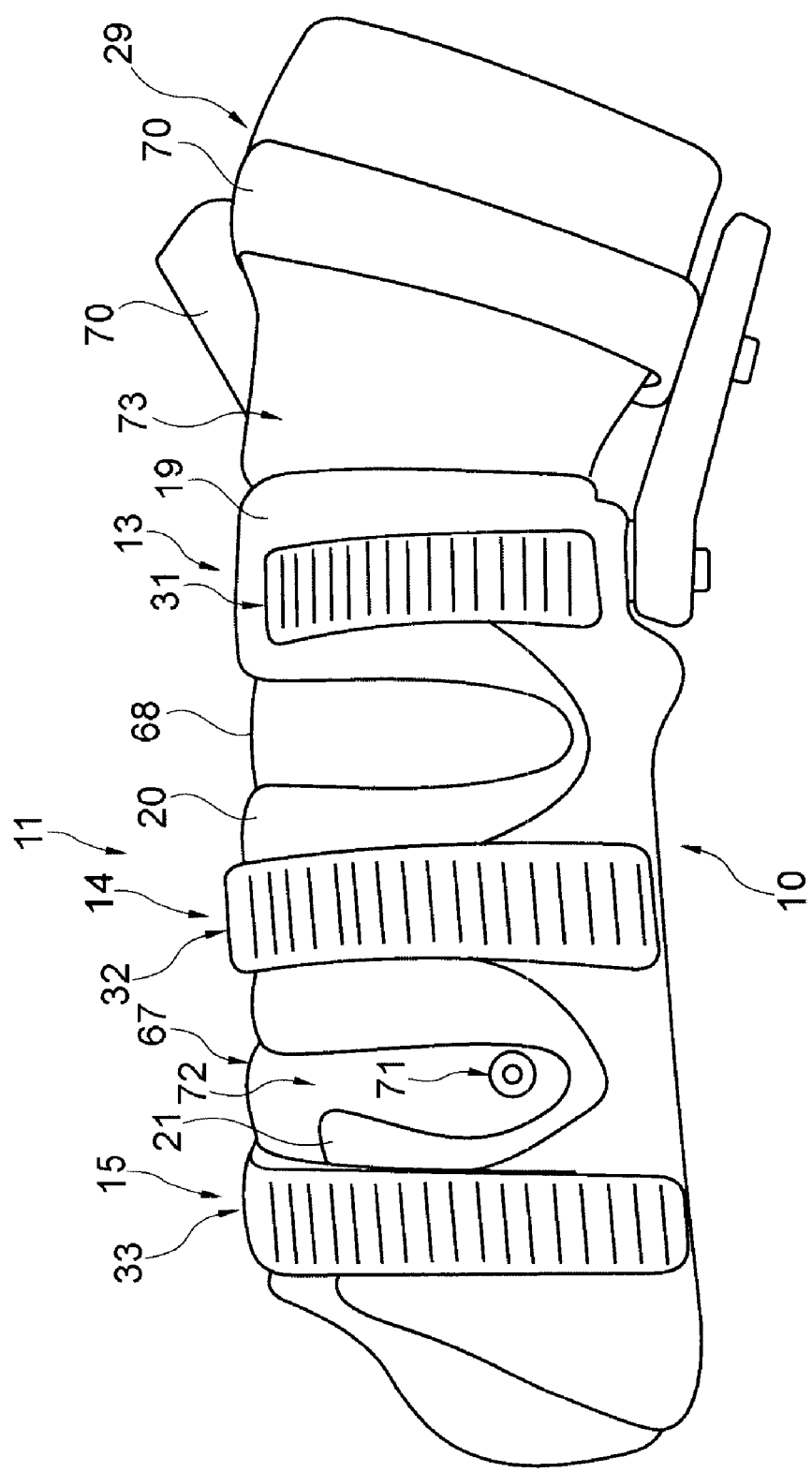
FIG. 7 the wrist orthosis shown in FIG. 6 in a dorsal view.

FIG. 1 shows a supporting shell 10 of a wrist orthosis 11 in a volar view, shown in its totality in FIGS. 6 and 7. As represented additionally by FIGS. 2 and 3 which show the supporting shell 10 in a dorsal view and an ulnar view, the supporting shell 10 is essentially constructed so that, as indicated clearly by the forearm contour shown in FIG. 1, a total of three pairs of straps 13, 14 and 15 are provided, starting from a supporting area 12 assigned to the elbow (ulna), each pair of straps having a volar strap 16, 17 and 18 assigned to the underside of the forearm and a dorsal strap 19, 20, 21 assigned to the top side of the forearm. As shown clearly by the ulnar view of the supporting shell 10, especially in FIG. 3, the supporting area 12 is designed like a backbone having a supporting strand 22 extending along the ulna, and dorsally and/or volarly therefrom, supporting ribs 23, 24, 25, each developing into a volar or dorsal strap 16 through 21, thereby forming stiffening reinforcements of the respective straps 16 through 21.

Figure 2:
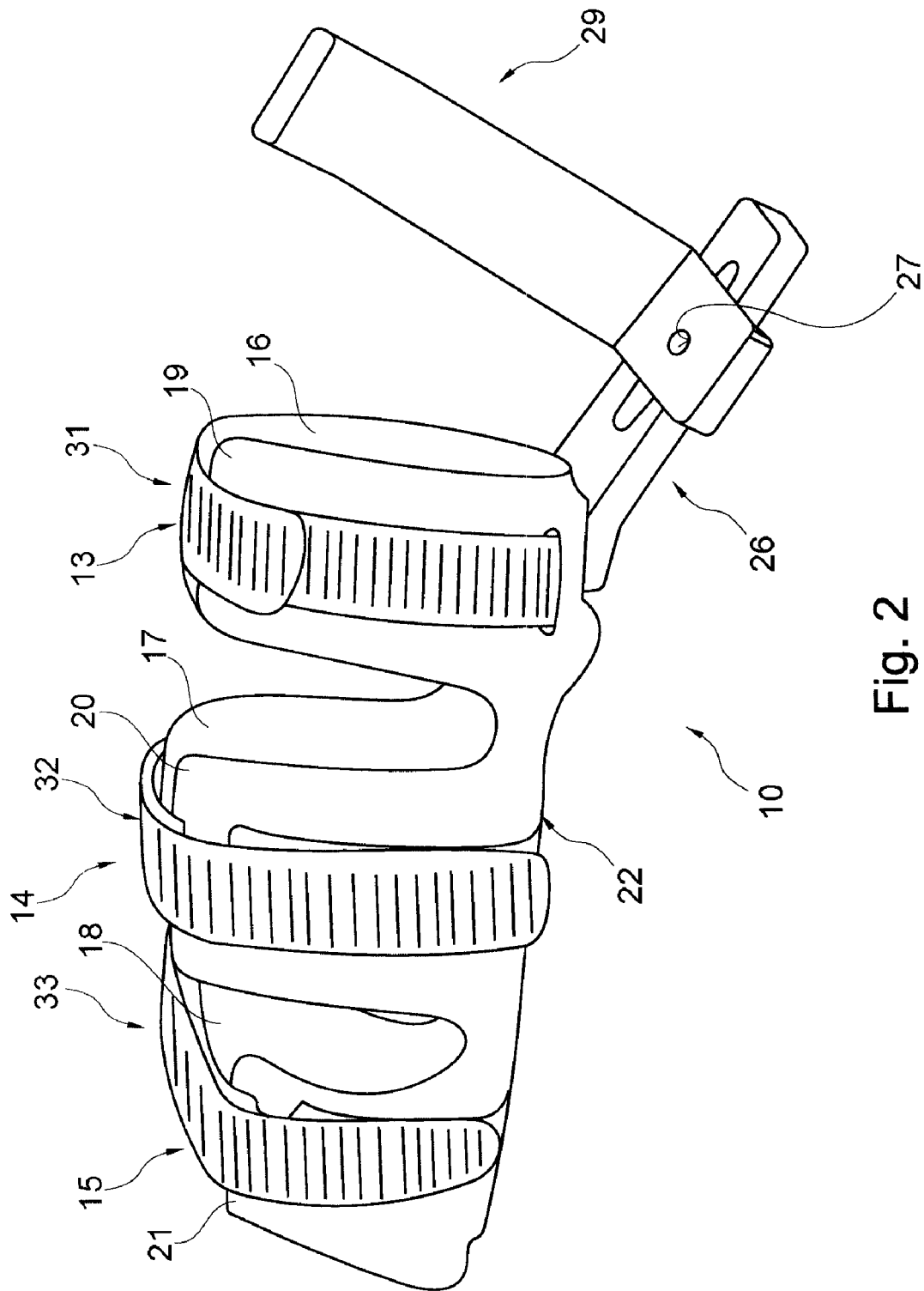
FIG. 2 the supporting shell shown in FIG. 1 in a dorsal view.
Figure 3:
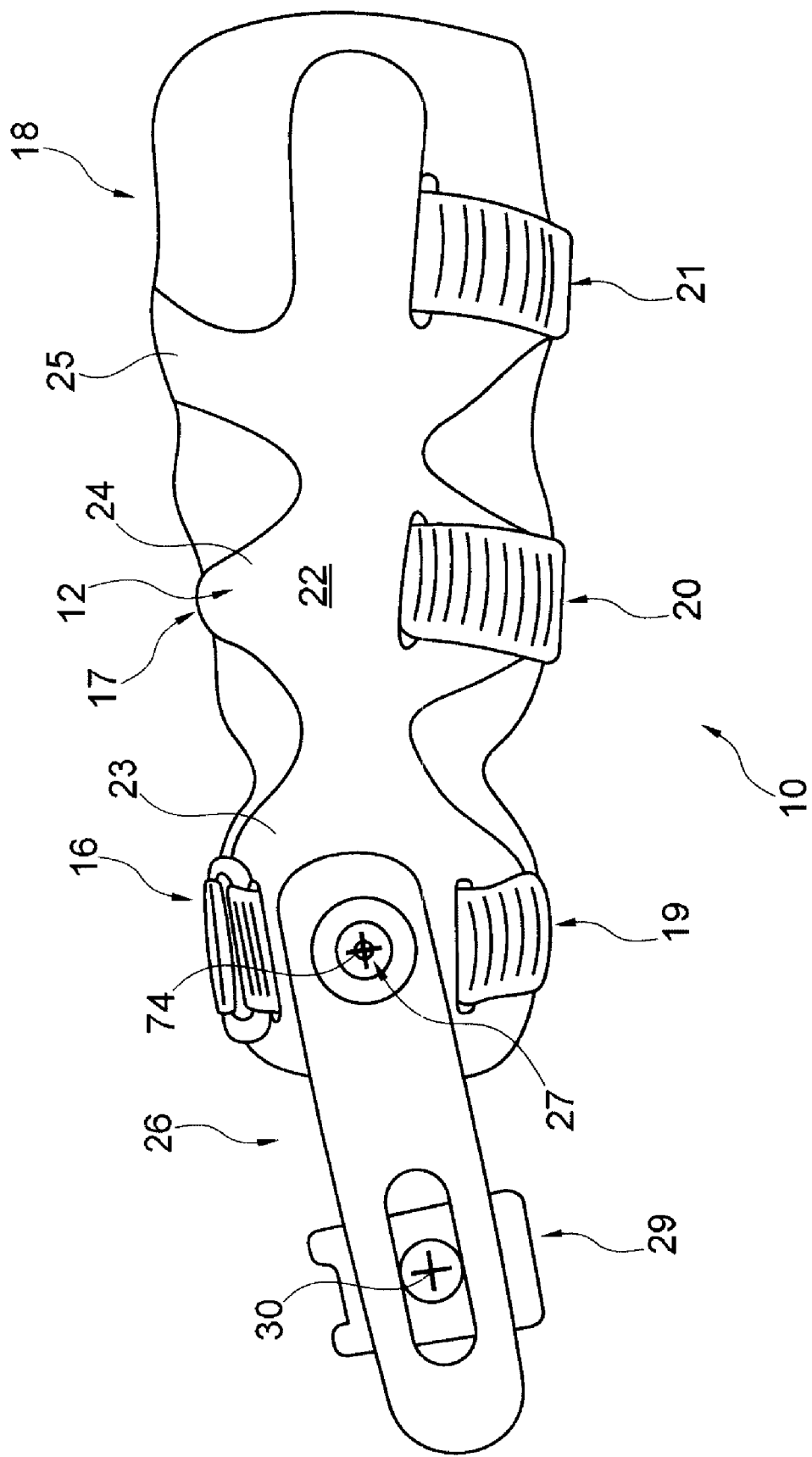
FIG. 3 the supporting shell shown in FIGS. 1 and 2 in an ulnar view.

As also shown in FIGS. 1 through 3, a cantilevered section 26 that is bent outward slightly at an angle from the elbow according to the contour of the hand is arranged on the distal end of the supporting area 12, its proximal end being connected to the distal end of the supporting strand 22 via a lockable swivel joint device 27 having a pivot axis 74 running coaxially with the axis of dorsal flexion. As shown in FIGS. 1 and 3 in particular, a hand support 29 is connected to the cantilevered portion 26 via a lockable sliding joint mechanism 28, the hand support serving to provide support against the palmar surface of the hand, permitting a relative displacement of the hand support 29 in the longitudinal direction of the cantilevered portion 26 as well as permitting rotation of the hand support 29 about a locking axis 30 of the sliding joint device 28. The hand support 29 has a contact plate 75 for support on the palmar surface of the hand. The contact plate 75 is adjustable with respect to a hand support base 76 by means of a lockable sliding joint device 77 to allow an adjustment of the hand support 29 to the respective width of the hand.

As shown by the diagram in FIG. 1, for example, the supporting shell 10 can be applied to the forearm by lateral displacement of the supporting shell 10 while at the same time spreading the pairs of straps 13 through 15 which are made of a dimensionally elastic plastic material and are connected in one piece to the supporting area 12. When the supporting shell 10 has been applied, the supporting area 12 of the supporting shell 10 is in contact with the forearm on the ulnar end and the hand support 29 is in contact with the palmar surface of the hand. As shown in FIG. 3 in particular, the pivotable deflection of the cantilevered section 26 on the supporting shell 10 by means of the swivel joint mechanism 27 allows the adjustment of a slight palmar flexion as needed, for example.

As is also clear from a combination of FIGS. 1, 2 and 3, the pairs of straps 13, 14, 15 are each provided with a closing device 31, 32, 33, which is designed here in the form of a VELCRO (a registered trademark) closure and makes it possible to pull the free ends of the straps 16, 19; 17, 20; 18, 21 of a pair of straps 13, 14, 15 toward one another to secure the supporting shell 10 in its applied position and to adjust the pressure acting on the forearm/wrist area by means of the pairs of straps 13, 14 and 15, depending on the tension acting on the closing devices 31, 32 and 33.

Figure 4:
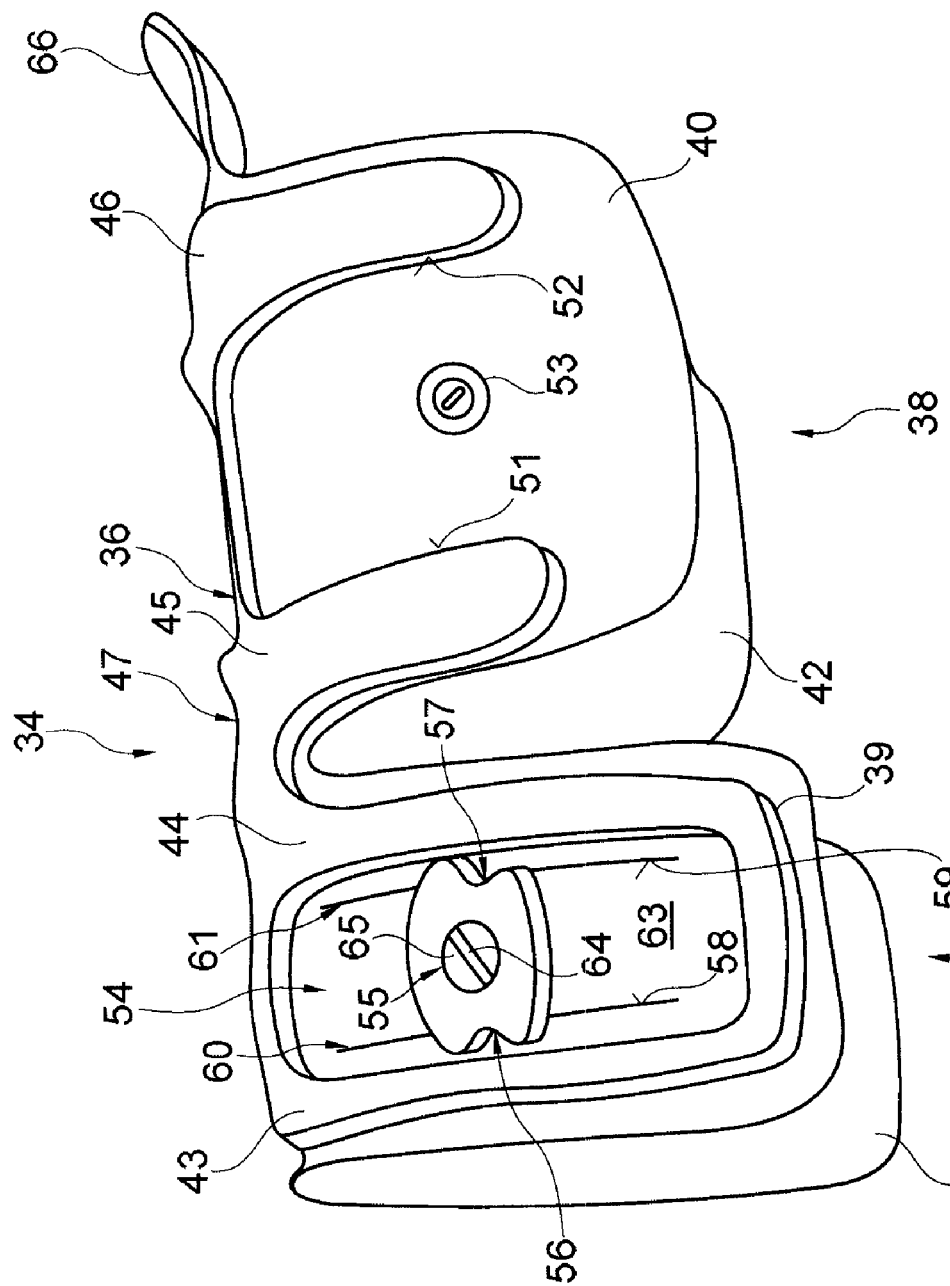
FIG. 4 a complementary shell for combination with the supporting shell depicted in FIGS. 1, 2 and 3.
Figure 5:
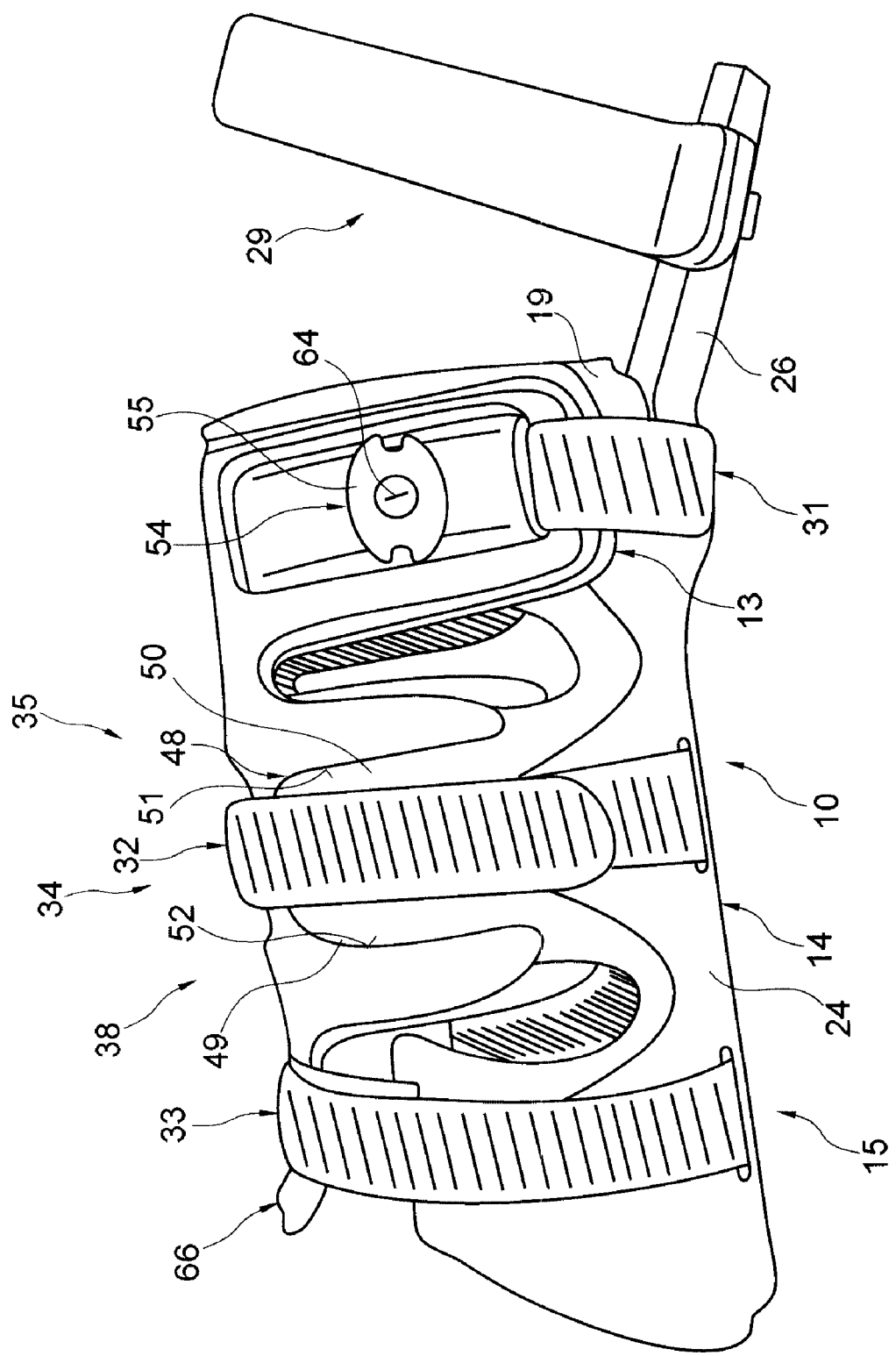
FIG. 5 the supporting shell supplemented by the complementary shell to form a circular design, shown here in a dorsal view.

FIG. 4 shows a complementary shell 34 made of a plastic material having dimensionally elasticity, which serves to supplement the supporting shell 10 in a circular form, as illustrated in FIG. 5, and thus forms a supporting shell arrangement 35 surrounding the forearm/wrist area on all sides. As FIG. 4 shows, the complementary shell 34 has a supporting area 36 which is provided with a distal and a proximal pair of straps 37, 38. The distal and proximal pairs of straps 37, 38 each comprise a volar strap 39 and/or 40 and a dorsal strap 41 and/or 42. The straps 39, 40 41, 42 each have two supporting ribs 43, 44 and/or 45, 46 which reinforce the straps, each rib leading away from a supporting strand 47 formed in the supporting area 36.

For a force-locking connection of the complementary shell 34 to the supporting shell 10, as shown in FIG. 5, an engaging connection 48 is formed between the proximal pair of straps of the complementary shell 34 and the central pair of straps 14 of the supporting shell 10, such that the volar strap 17 and the dorsal strap 20 of the central pair of straps 14 of the supporting shell 10 each engage at longitudinal edges 49, 50 of the straps with sliding guides 51, 52 formed on the longitudinal edges of the volar strap 40 and the dorsal strap 42 of the proximal pair of straps 38 of the complementary shell 34. As shown in FIG. 4 in particular, the sliding guides 51, 52 are formed by grooves parallel to the surface cut in the supporting ribs 45, 46 of the proximal pair of straps 38. A catch nub 53 formed on the strap surface of the volar strap 40 and the dorsal strap 42, engaging in a recess (not shown in detail in the figure) formed by shaping the supporting rib 24 of the straps 20 and 17 of the central pair of straps 14 of the supporting shell 10, ensures a loss-proof connection between the supporting shell 10 and the complementary shell 34 without having to use the closing devices 31, 32, 33 shown in FIG. 5 for this purpose.

As FIG. 4 shows, both the volar strap 39 and the dorsal strap 41 of the distal pair of straps 37 of the complementary shell 34 have a pressing mechanism 54 which comprises a sliding piece 55 which comprises, with a distal and proximal end area 56, 57, a guide edge 58, 59 of a strap slot 60, 61 running across the longitudinal extent. A bottom part (not shown in FIG. 4) is designed to correspond to the top part 62 of the sliding piece 55 shown in FIG. 4, and is in contact with a strap tongue 63 defined by the strap slots 60, 61 under an initial tension. Together with the contact of the sliding piece 55 with the strap tongue 63 under the initial tension, the connection of the end areas 56, 57 of the sliding piece 55 with the guide edges 58, 59 ensures a loss-proof connection between the sliding piece 55 and the straps 39, 41 of the distal pair of straps 37.

To change the initial tension with which the sliding piece 55 is in contact with the strap tongue 63, the sliding piece 55 is provided with a pressure screw 64, which is accommodated in a sliding piece thread (not shown here) of a sliding piece through-bore 65. The pressure screw 64, which is designed here in the manner of a headless screw, allows an increase in the initial tension between the sliding piece 55 and the strap tongue 63 by cutting into the through-bore 65 of the sliding piece 55 and thus permits a relative bulging of the strap tongue 63 in the direction of the wrist area. By displacement of the sliding piece 55 in relation to the guide edges 58, 59, the location of this bulge and thus the location where the pressure acts in the wrist area can be determined.

FIG. 5 shows that when the supporting shell 10 is supplemented by the complementary shell 34 to form a circular design, the pressing device 54 acts on the respective volar strap 16 and the dorsal strap 19 of the distal pair of straps 13 of the supporting shell 10. Furthermore, FIG. 5 shows that with the supporting shell arrangement 35 shown here, a supporting strand protrusion 66 designed on the proximal end of the complementary shell 34 is arranged radially opposite the proximal pair of straps 15 of the supporting shell 10 and can be connected in a force-locking manner to the pair of straps 15 by means of the closing mechanism 33 assigned to the proximal pair of straps 15.

FIGS. 6 and 7 show the wrist orthosis 11 in one possible configuration for application to the forearm/wrist area, illustrating the wrist orthosis 11 comprised of the supporting shell 10 and an evacuable molded cushion insert 67 that serves to line the supporting shell 10. The wrist orthosis 11 depicted in FIGS. 6 and 7 can be applied in two steps. In the first step, the molded cushion insert 67, shown in a planar development in FIG. 8, for example, and having a molded body filling (not shown in detail here) consisting of a plurality of preferably elastic molded bodies, and being provided with a textile covering 68 to increase the wearing comfort, is in contact with the patient's forearm/wrist area. A receiving opening 69 formed in the molded cushion insert 67 serves to allow the thumb to be passed through. The aerated molded cushion insert is then wrapped around the patient's forearm/ wrist area, forming a casing of the forearm/wrist area and secured in this relative arrangement by VELCRO closure devices (not shown in detail here) provided on the edges of the molded cushion insert. Then the thumb is passed through the receptacle 69 in the molded cushion insert 67 and is accommodated in a spigot 70 provided on the coating 68.

To supplement the molded cushion insert 67 applied to the forearm/wrist area with the supporting shell 10, the latter is pushed from the ulnar side onto the forearm/wrist area and there is an alignment and/or adjustment of the position of the hand support 29 to the patient's anatomy. Starting from this relative positioning of the supporting shell 10 on the forearm/wrist area by means of the dimensionally elastic design of the pairs of straps 13 through 15 of the supporting shell 10, there is a force-locking connection of the respective volar and dorsal straps 16, 17, 18 and/or 19, 20, 21 of the pairs of straps 13, 14, 15 by means of the closing devices 31, 32, 33 and there is a force-locking connection of the hand support 29 to the patient's hand by means of another closing device 70 designed here as a VELCRO closure provided on the hand support 29 as illustrated in FIGS. 6 and 7.

As FIG. 7 shows, the molded cushion insert 67 has a valve mechanism 71 for evacuation. The valve mechanism 71 may be arranged on the molded cushion insert 67 in such a way that with the arrangement of the supporting shell 10 combined with the molded cushion insert 67, the valve mechanism 71 comes to lie in a recess 72 formed between the dorsal strap 21 of the proximal pair of straps 15 and the dorsal strap 20 of the central pair of straps 14. By connecting a suitable evacuation device, e.g., a vacuum pump, the molded cushion insert 67, which has been flexible until that point, is secured in the configuration illustrated in FIG. 7. In conjunction with the outer support by the supporting shell 10, in the entire area of the supporting shell 10 and a metacarpal area 73 of the molded cushion insert 67 protruding beyond the distal end of the supporting shell 10, this therefore yields a dimensionally stable support for the forearm/wrist area that is adapted to the patient's anatomy, which in particular beyond the distal end of the supporting shell 10 i. e. also beyond the distal edge of the distal pair of straps 13, provides for accurate fixation of the relative position of the metacarpal area 73 with respect to the wrist.

As an alternative to the procedure described above, however, the molded cushion insert 67, which is advantageously accommodated in the textile covering 68, may also be arranged as a lining in the supporting shell 10 before applying the supporting shell, to then be pushed onto the forearm/wrist area subsequently along with the supporting shell 10.

Figure 8:
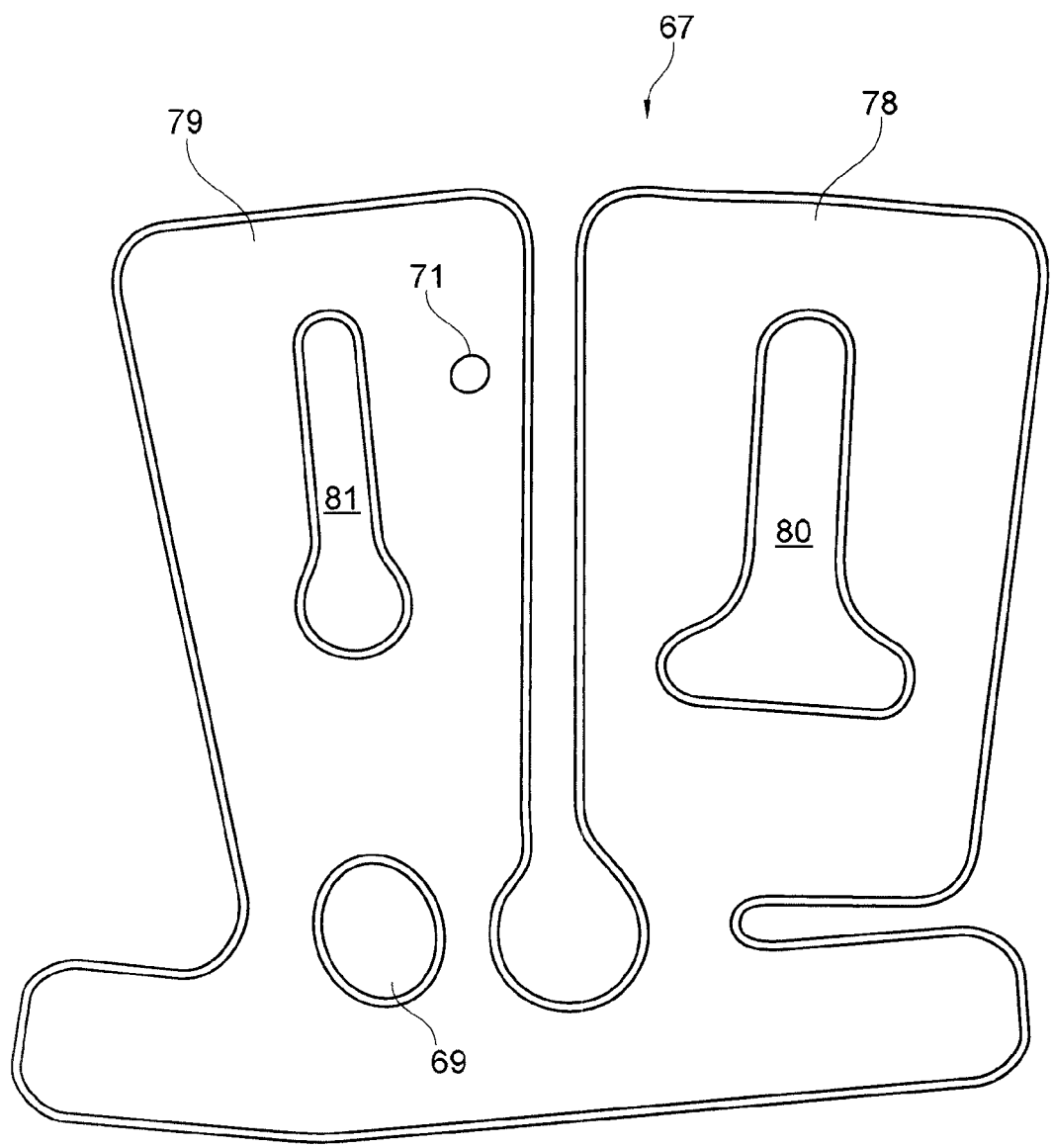
FIG. 8 the molded cushion insert shown here in FIGS. 6 and 7 in a planar development.

As shown by the blank cutout of the molded cushion insert 67 illustrated in FIG. 8 as an example, the molded cushion insert 67 has an ulnar insertion part 78 and a radial insertion part 79, starting from the metacarpal part 73 that is provided with the receptacle 69, said insertion parts being in contact with the forearm both ulnarly and radially and opposite one another when the molded cushion insert 67 is applied. In addition, the insertion parts 78, 79 are each provided with ventilation recesses 80, 81. The insertion parts 78, 79 have a relative arrangement and dimensioning so that there is no volar or dorsal overlap when the molded cushion insert 67 is applied.

Depending on the cause of the required stabilization of the wrist area, i.e., in the case of an ulnar fracture in the wrist area, for example, the supporting shell 10 can be supplemented in a circular design by the complementary shell 34, as illustrated in FIG. 5, supplemented by the lining of the supporting shell arrangement by the molded cushion insert as illustrated in FIGS. 6 and 7.

In the case of a circular configuration of the wrist orthosis that deviates from the diagram in FIGS. 6 and 7, the "after-pressure" effect, which is known from the conventional plaster cast treatment to achieve the associated advantages, can be achieved in this case by means of a suitable adjustment and/or relative positioning of the pressing device 54 as illustrated in FIG. 5, for example. When contrast medium is applied to the pressing device 54 and/or the sliding piece 55 or the pressure screw 64, it is also possible to verify by means of an X-ray whether the peak pressure achieved by pressing is also positioned accurately in relation to the fracture.

What is claimed:
1. A wrist orthosis comprising:
   a supporting shell that is open in a radial direction to receive a distal forearm area and having a volar hand support for coming into contact with a palmar surface of a hand and having a closing device for force-locking connection of the wrist orthosis to a wrist area; and a dimensionally stable supporting insert adapted to surround the wrist area to line the supporting shell and is designed to conform to the forearm area, the supporting insert extending beyond the supporting shell starting from a forearm part with a metacarpal part that covers a metacarpal area, wherein the supporting shell is provided on its distal end with a cantilevered portion that is adjustable in its relative arrangement for arrangement of the volar hand support.

2. The wrist orthosis according to claim 1, wherein the metacarpal part of the supporting insert is provided with a device for fixational alignment of the supporting insert on the thumb.

3. The wrist orthosis according to claim 1, wherein the supporting insert is made of an elastic plastic material.

4. The wrist orthosis according to claim 1, wherein the supporting insert is formed from an evacuable molded cushion insert with a molded body filling comprising a plurality of molded bodies.

5. The wrist orthosis according to claim 1, wherein ulnarly the supporting shell has a supporting area that is designed continuously, with at least one strap proceeding in the dorsal and volar directions therefrom.

6. The wrist orthosis according to claim 5, wherein the cantilevered portion is pivotably arranged on the supporting shell with a pivot axis running essentially coaxially with the axis of the dorsal flexion.

7. The wrist orthosis according to claim 1, further comprising a complementary shell for circular supplementation of the supporting shell, said complementary shell being open ulnarly and having a continuous supporting area radially, with at least one strap proceeding in dorsal and volar directions therefrom and said complementary shell being connectable in a force-locking manner to the supporting shell.

8. The wrist orthosis according to claim 7, wherein for force-locking connection of the complementary shell to the supporting shell, at least a partial overlap is provided between at least a first pair of straps comprising a volar strap and a dorsal strap of the supporting shell, and a second pair of straps comprising a dorsal strap and a volar strap of the complementary shell, and the closing device of the supporting shell serves for fixation of the overlap.

9. The wrist orthosis according to claim 8, wherein to establish the overlap between the first and second pairs of straps, an engagement is designed in such a way that the volar and dorsal straps of the supporting shell engage in a strap guide formed on the volar and dorsal straps of the complementary shell or vice versa.

10. The wrist orthosis according to claim 1, further comprising a complementary shell having distal and proximal pairs of straps wherein dorsal and volar straps of the distal pair of straps are provided with a pressing device which has a compressive force adjustment.

11. The wrist orthosis according to claim 10, wherein the pressing device is variable in its position relative to the dorsal and volar straps.

12. The wrist orthosis according to claim 11, wherein the pressing device is connected to the dorsal and volar straps in a radially displaceable manner.

\* \* \* \* \*